US005426183A

United States Patent [19]

Kjell

[11] Patent Number: 5,426,183

[45] Date of Patent: Jun. 20, 1995

[54] CATALYTIC STEREOSELECTIVE GLYCOSYLATION PROCESS FOR PREPARING 2'-DEOXY-2',2'-DIFLUORONUCLEOSIDES AND 2'-DEOXY-2'-FLUORONUCLEOSIDES

[75] Inventor: Douglas P. Kjell, West Lafayette, Ind.

[73] Assignee: Eli Lilly and Company, Indianapolis, Ind.

[21] Appl. No.: 44,312

[22] Filed: Apr. 7, 1993

Related U.S. Application Data

[63] Continuation-in-part of Ser. No. 902,112, Jun. 22, 1992, abandoned.

[51] Int. Cl.[6] .......... C07H 19/00

[52] U.S. Cl. .......... 536/28.55; 536/27.6; 536/27.61; 536/27.62; 536/27.63; 536/27.81; 536/28.1; 536/28.3; 536/28.4; 536/28.5; 536/28.51; 536/28.52; 536/28.53; 536/28.54

[58] Field of Search .......... 536/27.11, 27.21, 27.6, 536/28.1, 27.61, 27.62, 27.63, 28.81, 28.3, 28.4, 28.5, 28.51, 28.52, 28.53, 28.54, 28.55

[56] References Cited

U.S. PATENT DOCUMENTS

| | | | |
|---|---|---|---|
| 3,282,921 | 11/1966 | Verheyden et al. | 260/211 |
| 4,145,531 | 3/1979 | Eckstein et al. | 536/26 |
| 4,211,773 | 7/1980 | Lopez et al. | 424/180 |
| 4,526,988 | 7/1985 | Hertel | 549/313 |
| 4,625,020 | 11/1986 | Brundidge et al. | 536/18 |
| 4,751,221 | 6/1988 | Watanabe et al. | 514/46 |
| 4,965,374 | 10/1990 | Chou et al. | 549/313 |
| 5,075,446 | 12/1991 | Kim et al. | 544/316 |

FOREIGN PATENT DOCUMENTS

| | | | |
|---|---|---|---|
| 145978 | 6/1985 | European Pat. Off. | C07H 13/00 |
| 211354 | 2/1987 | European Pat. Off. | C07H 19/073 |
| 219829 | 4/1989 | European Pat. Off. | C07H 19/16 |
| 339161 | 11/1989 | European Pat. Off. | C07F 9/65 |
| 345751 | 12/1989 | European Pat. Off. | A61K 31/70 |
| 428109 | 5/1991 | European Pat. Off. | C07H 19/19 |
| 2125401 | 3/1984 | United Kingdom | C07D 405/04 |

OTHER PUBLICATIONS

Vorbruggen, et al., *J. Org. Chem., 41(12), 2084–2086 (1976).*

Walker, et al., *Nucleic Acid Research,* 12(17), 6827–37 (1984).

R. P. Hodge, et al., *J. Org. Chem.,* 56, 1553–64 (1991).

Tann, et al., *J. Org. Chem.,* 50, 3644–47 (1985).

Howell, et al., *J. Org. Chem.,* 53, 85–88 (1988).

Hoffer, et al., *Chem. Ber.,* 93, 2777–81 (1960).

*Primary Examiner*—Douglas W. Robinson
*Assistant Examiner*—J. Oliver Wilson
*Attorney, Agent, or Firm*—Robert A. Conrad; David E. Boone

[57] ABSTRACT

A catalytic stereoselective glycosylation process for preparing beta- and alpha-anomer enriched 2'-deoxy-2',2'-difluoronucleosides and 2'-deoxy-2'-fluoronucleosides involving reacting an alpha- or beta- anomer enriched 2-deoxy-2,2-difluorocarbohydrate or 2-deoxy-2-fluorocarbohydrate with at least a molar equivalent of a nucleobase derivative in an inert solvent and in the presence of a catalyst.

24 Claims, No Drawings

CATALYTIC STEREOSELECTIVE GLYCOSYLATION PROCESS FOR PREPARING 2'-DEOXY-2',2'-DIFLUORONUCLEOSIDES AND 2'-DEOXY-2'-FLUORONUCLEOSIDES

CROSS REFERENCE TO RELATED APPLICATION

This application is a continuation-in-part of Ser. No. 07/902,112 filed Jun. 22, 1992 now abandoned.

BACKGROUND OF THE INVENTION

1. Field of the Invention

The invention pertains to the field of pharmaceutical chemistry and provides a catalytic stereoselective glycosylation process for preparing 2'-deoxy-2',2'-difluoronucleosides and 2'-deoxy-2'-fluoronucleosides.

2. State of the Art

The continued interest in the synthesis of 2'-deoxynucleosides and their analogues is reflected in their successful use as therapeutic agents in viral and cancerous diseases. A critical step in the synthesis of 2'-deoxynucleosides is the condensation of the nucleobase and carbohydrate to form the N-glycosidic bond. When the carbohydrate possesses a 2-hydroxy substituent, the substituent provides a substantial degree of 1,2-anchiomeric assistance, which facilitates stereoselective glycosylation. However, processes for synthesizing of 2'-deoxynucleosides are typically non-stereoselective and form a mixture of alpha and beta nucleosides.

Vorbruggen, et al., *J. Org. Chem.,* 41, 2084 (1976) provided an outstanding development in the field of glycosylation and showed how nucleosides may be obtained from the Friedel-Crafts catalyzed reaction of a peracylated carbohydrate and silylated heterocycles in a solvent such as 1,2-dichloroethane or acetonitrile. But when this process was applied to the synthesis 2'-deoxynucleosides, a 1:1 alpha to beta-anomeric mixture of nucleoside products was produced.

Some deoxynucleosides have been prepared in high yield from deoxyhalogenose with Friedel-Crafts catalysts, notably, 1-chloro-2-deoxy-3,5-di-p-toluoyl-alpha-D-erythropentofuranose, see, M. Hofer, *Chem. Ber,* 93, 2777 (1960). However, halogenoses are less stable thermally than peracylated carbohydrates and produce a 1:1 alpha to beta-anomeric mixture of nucleoside products. Walker, et al., *Nucleic Acid Research,* 12, 6827 (1984), used halogenose in condensation reactions to study the factors controlling the anomeric ratio of nucleoside products and found that beta-anomer nucleosides were formed exclusively from alpha-halocarbohydrates via $S_N2$ displacement. The corresponding alpha-anomer nucleoside contamination was determined to result from the anomerization of alpha-halo carbohydrate to beta-halo carbohydrate before the $S_N2$ displacement reaction. Walker, et al., found that by changing the solvent or catalyst higher yields of the desired betaanomer nucleoside were produced.

R. P. Hodge et. al., *J. Org. Chem.,* 56, 1553 (1991), described preparing pyrimidine and purine nucleosides containing deuterium at the C-1' position by the method described by Walker, et al. 1'-Deuterium-2'-deoxycytidine was prepared by reacting a carbohydrate and silylated cytosine derivative but the reaction gave poor yields. However, the yield was significantly improved when silylated uridine derivatives were used.

U.S. Pat. No. 5,075,446, Kim, et. al., describes a process for coupling a trimethylsilylated pyrimidine base with 2-acetoxytetrahydrofuran using a catalytic amount of cesium chloride in acetonitrile under mild conditions.

The synthesis of 2'-deoxy-2'-fluoroarabinofuranosyl nucleosides advanced rapidly when a procedure for synthesizing 2-deoxy-2-fluoro-3,5-di-O-benzoyl-alpha-D-arabinosyl bromide was made available; see Tann, et. al., *J. Org. Chem.,* 50, 3644 (1985) and Howell, et. al., *J. Org. Chem.,* 53, 85 (1988). It was discovered that 2-deoxy-2-fluoro-3,5-di-O-benzoyl-alpha-D-arabinosyl bromide did not anomerize in dry acetonitrile over extended periods. Therefore, high yields of beta-nucleosides could be obtained from 2-deoxy-2-fluoro-3,5-di-O-benzoyl-alpha-O-arabinosyl bromide via $S_N2$ displacement. Also, stereoselectivity of the nucleoside products could be achieved if either carbon tetrachloride or chloroform solvents was employed.

The formation of the N-glycoside bond in 2'-deoxy-2',2'-difluoronucleoside synthesis is much more difficult than in instances where the carbohydrate is 1,2-anchiometric assisted or contains only 1 fluorine at the C-2 position. The traditional carbohydrate leaving groups used in the Vorbruggen condensation method such as acetate, chloride and bromide, render the carbohydrate inactive. In order to overcome this problem, Hertel, U.S. Pat. No. 4,526,988, described a modified version of the Vorbruggen condensation method that relied on more reactive sulfonate leaving groups attached to the carbohydrate to affect its reactivity. For example, hydroxy protected carbohydrates, such as 2-deoxy-2,2-difluoro-D-ribofuranose, containing a methanesulfonate, toluenesulfonate, ethanesulfonate, isopropanesulfonate or 4-methoxybenzenesulfonate leaving group at the C-1 position, were reacted with a protected nucleobase at temperatures of 50° C. to 220° C., in the presence of a high boiling solvent, such as dimethylformamide, dimethylacetamide and hexamethylphosphoramide. Hertel teaches that when carrying out the glycosylation reaction at elevated pressures, any convenient inert solvent, such as ethers, halogenated alkanes, and aromatics, can be used since the elevated pressure eliminates the loss of low boiling inert solvents due to evaporation. However, at reaction temperatures from room temperature to 100° C., a catalyst such as trifluoromethanesulfonyloxysilane is required.

U.S. Pat. No. 4,965,374, Chou, et al., reports that Hertel's condensation method produces a 4:1 alpha to beta anomer ratio of nucleoside products and goes on to describe an improved procedure, based on the Vorbruggen condensation method, that employs a pivotol intermediate of 2-deoxy-2,2-difluoro-3,5-di-O-benzoyl-alpha-D-arabinosyl methanesulfonate and a trimethylsilyltrifluoromethanesulfonate catalyst. However, Chou's method forms a 1:1 alpha to beta anomer mixture of nucleoside products.

Despite the processing advances in nucleoside synthesis, there continues to be a need for a catalytic stereoselective glycosylation process capable of efficiently producing beta- or alpha-anomer enriched 2'-deoxy-2',2'-difluoronucleosides and 2'-deoxy-2'-fluoronucleosides in increased yields.

Accordingly, one object of the present invention is to provide a stereoselective glycosylation process for efficiently preparing beta- or alpha-anomer enriched 2'-deoxy-2',2'-difluoronucleosides and 2'-deoxy-2'-fluoronucleosides.

Another object of the present invention is to provide a catalytic stereoselective glycosylation process for preparing beta- or alpha-anomer enriched 2'-deoxy-2',2'-difluoronucleosides and 2'-deoxy-2'-fluoronucleosides that requires reduced amounts of nucleobase derivative.

Other objects and advantages of the present invention will become apparent from the following description of embodiments.

SUMMARY OF THE INVENTION

The invention is a catalytic stereoselective glycosylation process for preparing a beta-anomer enriched nucleoside of the formula

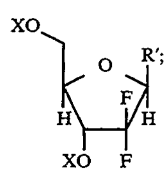

wherein each X is independently selected from hydroxy protecting groups and R' is a nucleobase selected from the group consisting of

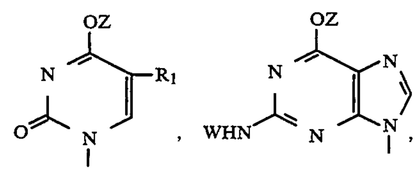

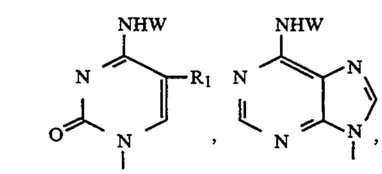

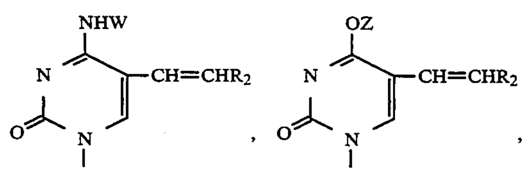

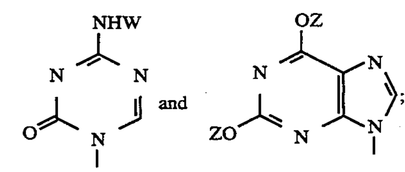

wherein $R_1$ is selected from the group consisting of hydrogen, alkyl and halo; $R_2$ is selected from the group consisting of hydrogen, alkyl and halo; Z is a hydroxy protecting group; and W is an amino protecting group; comprising reacting an alpha-anomer enriched 2,2-diflurocarbohydrate of the formula

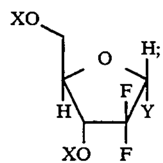

wherein Y is selected from the group consisting of alkylsulfonyloxy, arylsulfonyloxy, substituted alkylsulfonyloxy and substituted arylsulfonyloxy and X is as defined above; with at least a molar equivalent of a nucleobase derivative, R", selected from the group consisting of

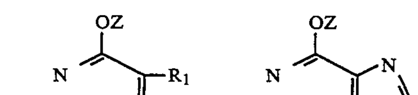

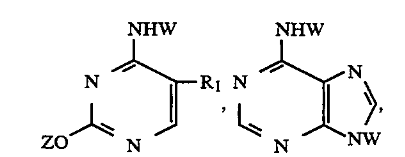

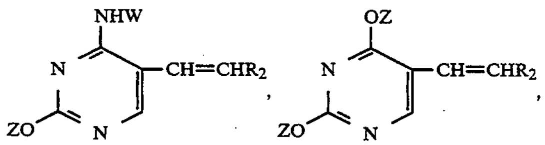

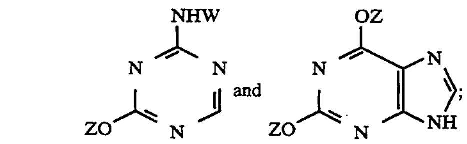

wherein $R_1$, $R_2$, Z and W are as defined above; in an inert solvent and in the presence of a catalyst.

In another aspect, the invention is a catalytic stereoselective glycoslation process for preparing an alpha-anomer enriched nucleoside of the formula

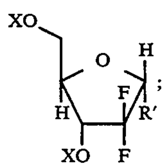

wherein X and R' are as defined above; comprising reacting a beta-anomer enriched 2,2-difluorocarbohydrate of the formula

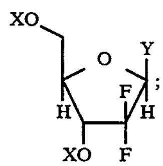

wherein X and Y are as defined above; with at least a molar equivalent of a nucleobase derivative, R", in an inert solvent and in the presence of a catalyst.

In another aspect, the invention is a catalytic stereoselective glycosylation process for preparing a betaanomer enriched nucleoside of the formula (IVB)

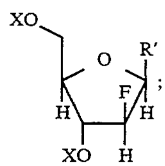

wherein X and R' are as defined above comprising reacting an alpha-anomer enriched 2-fluorocarbohydrate of the formula (VA)

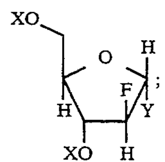

wherein Y and X are as defined above with at least a molar equivalent of a nucleobase derivative, R", in an inert solvent and in the presence of a catalyst.

In another aspect the invention is a catalytic stereoselective glycoslation process for preparing an alpha-anomer enriched nucleoside of the formula (IVA)

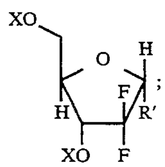

wherein X and R' are as defined above; comprising reacting a beta-anomer enriched 2-fluorocarbohydrate of the formula (VB)

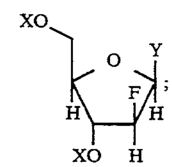

wherein x and Y are as defined above; with at least a molar equivalent of a nucleobase derivative, R", in an inert solvent and in the presence of a catalyst.

The invention also provides a catalytic stereoselective glycosylation process for preparing a beta-anomer enriched nucleoside of the formula (VIB)

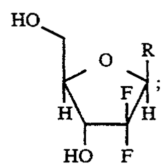

wherein R is a deblocked nucleobase selected from the group consisting of

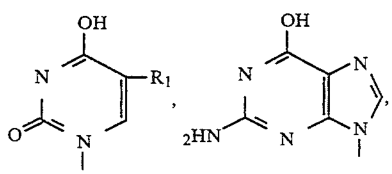

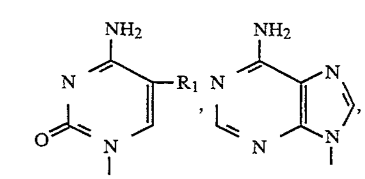

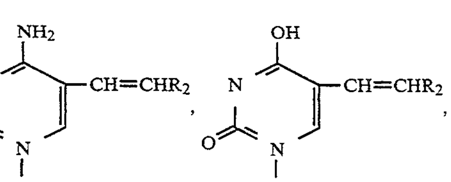

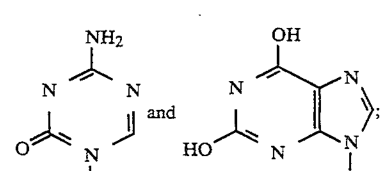

wherein $R_1$ is selected from the group consisting of hydrogen, alkyl and halo; $R_2$ is selected from the group consisting of hydrogen, alkyl and halo; comprising reacting an alpha-anomer enriched 2,2-difluorocarbohydrate of the formula (IIA)

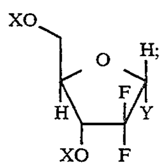

wherein Y is selected from the group consisting of alkylsulfonyloxy, arylsulfonyloxy, substituted alkylsulfonyloxy and substituted arylsulfonyloxy and each X is a hydroxy protecting group; with at least a molar equivalent of a nucleobase derivative, R", selected from the group consisting of

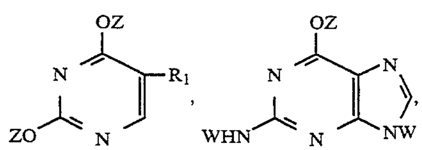

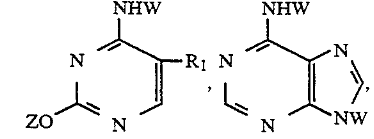

-continued

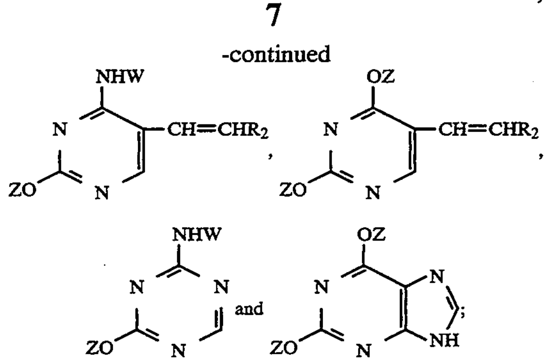

wherein $R_1$ and $R_2$ are as defined above; Z is a hydroxy protecting group; and W is an amino protecting group; in an inert solvent and in the presence of a catalyst; and deblocking.

Also provide is a catalytic stereoselective glycosylation process for preparing a beta-anomer enriched 2-fluoro nucleoside of the formula

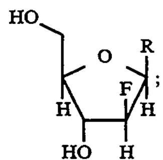

(VIIB)

wherein R is a deblocked nucleobase as defined above; comprising reacting an alpha-anomer enriched 2-fluorocarbohydrate of the formula

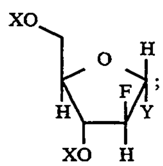

(VA)

wherein Y and X are as defined above; with at least a molar equivalent of a nucleobase derivative, R″, wherein R″ is as defined above; in an inert solvent; in the presence of a catalyst; and deblocking.

Also provided is a catalytic stereoselective glycosylation process for preparing an alpha anomer enriched nucleoside of the formula

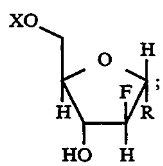

(VIIA)

wherein R is a deblocked nucleobase as defined above; comprising reacting a concentrated beta-anomer enriched 2,2-difluorocarbohydrate of the formula

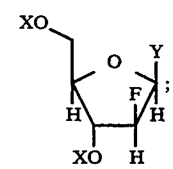

(VB)

wherein Y is selected from the group consisting of arylsulfonyloxy, substituted arylsulfonyloxy and each X is a hydroxy protecting group; with at least a molar equivalent of a nucleobase derivative, R″, wherein R″ is as defined above; in an inert solvent and in the presence of a catalyst; and deblocking.

Also provided is a catalytic stereoselective glycosylation process for preparing an alpha-anomer enriched nucleoside of the formula

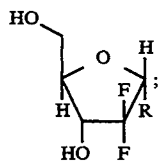

(VIA)

wherein R is a deblocked nucleobase as defined above; comprising reacting a concentrated beta-anomer enriched 2,2-difluorocarbohydrate of the formula

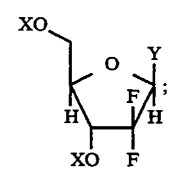

(IIB)

wherein Y is selected from the group consisting of arylsulfonyloxy, substituted arylsulfonyloxy and each X is a hydroxy protecting group; with at least a molar equivalent of a nucleobase derivative, R″, wherein R″ is as defined above; in an inert solvent and in the presence of a catalyst; and deblocking.

DETAILED DESCRIPTION OF THE INVENTION

Throughout this document, all temperatures are in degrees Celsius, all proportions, percentages and the like, are in weight units and all mixtures are in volume units, except where otherwise indicated. Anomeric mixtures are expressed as a weight/weight ratio or percent. The term "lactol" alone or in combination refers to a 2-deoxy-2,2-difluoro-D-ribofuranose or 2-deoxy-2-fluoro-D-ribofuranose. The term "carbohydrate" alone or in combination refers to an activated lactol wherein the hydroxy group at the C-1 position has been replaced by a desirable leaving group. The term "halo" alone or in combination refers to chloro, iodo, fluoro and bromo. The term "alkyl" alone or in combination refers to straight, cyclic and branched chain aliphatic hydrocarbon groups which preferably contain up to 7 carbon atoms such as methyl, ethyl, n-propyl, isopropyl, n-butyl, t-butyl, n-pentyl, n-hexyl, 3-methylpentyl groups and the like or halo substituted straight, cyclic and branched chain aliphatic hydrocarbons such as chloroethyl, 1,2-dichloroethyl and the like. The term "alkoxy" alone or in combination refers to compounds of the general formula AO; wherein A is alkyl. The term "aryl" alone or in combination refers to carbocyclic or heterocyclic groups such as phenyl, naphthyt and substituted derivatives thereof. The term "aromatic" alone or in combination refers to benzene-like structures containing $(4\pi+2)$ delocalized $\pi$ electrons. The terms "sulfonate" or "sulfonyloxy" alone or in combination refer to compounds of the general formula $BSO_3$; wherein B is alkyl or aryl. The term "substituted" alone or in combination refers to the replacement of hydrogen or a common moiety by one or more of the groups selected from cyano, halo, carboalkoxy, toluoyl, nitro, alkoxy, alkyl, and dialkyl amino. The phrase "anomer-enriched" alone or in combination refers to an anomeric mixture wherein the ratio of a specified anomer is greater than 1:1 and includes a substantially pure anomer.

In accordance with the present stereoselective catalytic glycosylation process, beta-anomer enriched 2'-deoxy-2',2'-difluoronucleosides and 2'deoxy-2'-fluoronucleosides of formulas I and IV are prepared by reacting an alpha-anomer enriched carbohydrate of formulas II and V with at least a molar equivalent of a nucleobase derivative in an inert solvent and in the presence of a catalyst, as shown in the following reaction schemes for making beta-anomer enriched nucleosides:

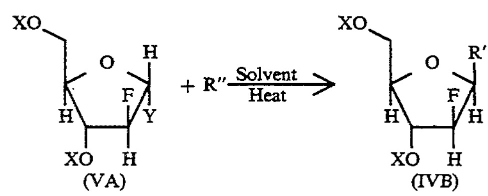

and

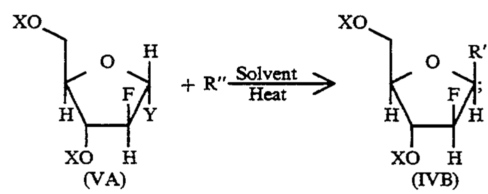

wherein Y, X, R" and R' are as defined above. While not wishing to be bound by theory, it is believed that the glycosylation reaction proceeds via an $S_N2$ displacement. Therefore, the beta-anomer enriched nucleoside products are derived from alpha-anomer enriched carbohydrates. Conversely, the alpha-anomer enriched nucleoside products are derived from beta-anomer enriched carbohydrates.

The lactol starting materials suitable for use in the present glycosylation process are commonly known in the art and can be readily synthesized by standard procedures commonly employed by those of ordinary skill in the art. For example, U.S. Pat. No. 4,526,988 teaches the synehteis of 2,2-difluoro-2-deoxy-D-ribofuranoses having the formula

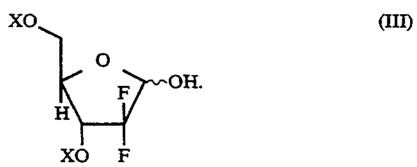

In addition, Reichman, et al., *Carbohydr. Res.*, 42, 233 (1975) teaches the synthesis of 2-deoxy-2-fluoro-D-ribofuranoses of the formula

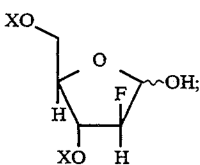

In a preferred embodiment, a 2,2-difluoro-2-deoxy-D-ribofuranose-3,5-dibenzoate of formula III is used to prepare blocked nucleoside products under the present invention.

Glycosylation reactions typically require protecting the oxygen atoms of the hydroxy groups of the lactol of formulas III and VI to prevent the hydroxy groups from reacting with the nucleobase derivative, or being decomposed in some manner. Hydroxy protecting groups (X) suitable for use in the present glycosylation process may be chosen from known protecting groups used in synthetic organic chemistry. Each hydroxy protecting group selected is preferably capable of being efficiently placed on the lactol and easily removed therefrom once the glycosylation reaction is completed. Hydroxy protecting group known in the art are described in Chapter 3 of *Protective Groups in Organic Chemistry*, McOmie Ed., Plenum Press, New York 1973), and Chapter 2 of *Protective Groups in Organic Synthesis*, Green, John, J. Wiley and Sons, New York (1981); preferred are ester forming groups such as formyl, acetyl, substituted acetyl, propionyl, butynyl, pivaloyl, 2-chloroacetyl, benzoyl, substituted benzoyl, phenoxycarbonyl, methoxyacetyl; carbonate derivatives such as phenoxycarbonyl, ethoxycarbonyl, t-butoxycarbonyl, vinyloxycarbonyl, 2,2,2-trichloroethoxycarbonyl and benzyloxycarbonyl; alkyl ether forming groups such as benzyl, diphenylmethyl, triphenylmethyl, t-butyl, methoxymethyl, tetrahydropyranyl, allyl, tetrahydrothienyl, 2-methoxyethoxy methyl; and silyl ether forming groups such as trialkylsilyl, trimethylsilyl, isopropyldialkylsilyl, alkyldiisopropylsilyl, triisopropylsilyl, tbutyldialkylsilyl and 1,1,3,3-tetraisopropyldisloxanyl; carbamates such as N-phenylcarbamate and N-imidazoylcarbamate; however more preferred are benzoyl, mono-substituted benzoyl and disubstituted benzoyl, acetyl, pivaloyl, triphenylmethyl ethers, and silyl ether forming groups, especially t-butyldimethylsilyl; while most preferred is benzoyl.

In attaching each hydroxy protecting group to the lactol, typical reaction conditions are employed which depend on the nature of the protecting group chosen. Typical reaction conditions for attaching hydroxy protecting groups to lactols are discussed in U.S. Pat. No. 4,526,988 which is incorporated herein by reference.

To obtain an efficient reaction of the nucleobase derivative and carbohydrate, an appropriate leaving group is stereoselectively attached to the lactol of formulas III and VI which activates the lactol and generates the beta- and alpha-anomer enriched carbohydrate of formulas II and V. The leaving group (Y) of the carbohydrate may be selected from the group consisting of alkylsulfonyloxy, arylsulfonyloxy and substituted alkylsulfonyloxy and substituted arylsulfonyloxy; provided that highly fluorinated groups such as trifluoromethanesulfonyloxy and 1,1,1-trifluoroethanesulfonyloxy, are not used; however, more preferred leaving groups are methanesulfonyloxy, 2-chloroethanesulfonyloxy, toluenesulfonyloxy, p-nitrobenzenesulfonyloxy and p-bromobenzenesulfonyloxy; while most preferred is methanesulfonyloxy.

The alpha-anomer enriched carbohydrate of formula II may be prepared by one of three methods. The alpha-anomer enriched carbohydrate of formula V is prepared by the third of these methods. The first method is described in U.S. Pat. No. 5,256,798 No.07/902,305, and teaches treating a beta-anomer ribofuranosyl sulfonate or anomeric mixture thereof with a source of a conjugate anion of a sulfonic acid at elevated temperatures in an inert solvent. The second method, described in pending U.S. Pat. application Ser. No.07/902,301, teaches reacting a lactol such as that of formulas III and VI with an amine base such as triethylamine, tributylamine, dibutylamine, diethylmethylamine, dimethylethylamine, benzylmethylamine, N-methylmorpholine, tripropylamine, dipropylethylamine, N,N-dimethytbenzylamine, diisopropylethylamine, diethylamine, 1,8-diazabicyclo[5.4.0]undec-7-ene and 1,5-diazobicyclo[4.3.0]non-5-ene. The amine preferably has a pKa from about 8 to about 20 and is employed in a range of from about 1 molar equivalent to about 2 molar equivalents and more preferably from about 1.2 molar equivalents to about 1.5 molar equivalents. The reaction is carried out in an inert solvent having a freezing point temperature preferably below −78° C. Preferred solvents are selected from the group consisting of dichloromethane, 1,2-dichloroethane, dichlorofluoromethane, acetone, toluene, anisole, chlorobenzene, and mixtures thereof. The temperature of the mixture is adjusted preferably in the range from about −40° C. to about −120° C. and more preferably below about −78° C. While not wishing to be bound by theory it is believed that the low temperature shifts the alpha to beta anomeric ratio of the lactol in favor of the alphaanomer in a range of from about 2:1 to about 4:1 alpha to beta. For example, a compound of formula III, where X is benzoyl, was added to dichloromethane and triethylamine at room temperature for 30 minutes. Next, the temperature of the reaction mixture was lowered. An $^{19}F$ NMR, taken at various temperatures, shows an increase in the alpha to beta ratio of the ionized lactol as the temperature was lowered:

| Temperature | Alpha/Beta Ratio |
|---|---|
| 19° C. | 2.0:1 |
| −3° C. | 2.3:1 |
| −23° C. | 2.5:1 |
| −43° C. | 3.0:1 |
| −63° C. | 3.6:1 |
| −83° C. | 4.4:1 |

The ionized lactol was then trapped in solution at the low temperature and higher alpha-anomer ratio by adding a sulfonating reagent which forms an alpha-anomer enriched carbohydrate.

The sulfonating reagents are selected from the group consisting of substituted and unsubstituted alkyland aryl-sulfonyloxy halides and sulfonic acid anhydrides, depending on the leaving group desired.

A method for preparing the beta-anomer enriched carbohydrates of formula II is described in U.S. Pat. No. 5,252,756. The method requires reacting a lactol of formula III with an arylsulfonyl halide or arylsulfonyl anhydride such as toluenesulfonyl chloride, benzenesulfonyl chloride and p-bromobenzenesulfonyl chloride, in the presence of an amine base such as triethylamine.

The beta- or alpha-anomer enriched carbohydrates may be isolated in substantially pure form; i.e., greater than 95 percent purity; by the procedure described in U.S. Pat. No. 5,256,797. The method involves warming an anomeric mixture of the carbohydrates in a solvent from about 30° C. to about 70° C. to form a supersaturated solution. The solvent may be selected from the group consisting of 1,2-dichloroethane, anisole, glyme, and mixtures thereof. The carbohydrate forms a precipitate when the temperature of the solution is lowered to about 10° C. and a counter solvent is added. The counter solvent may be selected from the group consisting of methanol, ethanol, toluene, ether, dichloromethane, and mixtures thereof. The resulting carbohydrate crystals are then recovered from the solution and dried.

The nucleobases (R′) employed herein are commonly known to organic chemists and no discussion of their synthesis is necessary. However, in order to be useful in the present glycosylation process, nucleoside derivatives or their tautomeric equivalents bearing amino or hydroxy groups preferably contain protecting group, such as primary amino protecting groups (W) and/or hydroxy protecting groups (Z), depending on the nature of the nucleobase derivative selected. The protecting group blocks the hydroxy or amino groups which may provide a competing reaction site for the beta- or alpha-anomer carbohydrate. The protecting groups are attached to the nucleobase derivative (R′) which is reacted with the beta-or alpha-anomer enriched carbohydrate of formulas II and V and are removed subsequent thereto. A procedure for protecting nucleobase derivatives is described in U.S. Pat. No. 4,526,988.

Preferred amino protecting groups (W) for pyrimidine nucleobase derivatives are selected from the group consisting of silyl ether forming groups such as trialkylsilyl, t-butyldialkylsilyl and t-butyldiarylsilyl; carbamates such as t-butoxycarbonyl, benzyloxycarbonyl, 4-methoxybenzyloxycarbonyl, and 4-nitrobenzyloxycarbonyl; formyl, acetyl, benzoyl and pivalamido; ether forming groups such as methoxymethyl, t-butyl, benzyt, allyl and tetrahydropyranyl; more preferred is trimethylsilyl. Preferred amino protecting groups (W) for purine nucleobase derivatives are selected from the group consisting of alkylcarboxamides, haloalkylcarboxamides and arylcarboxamides such as 2-trialkylsilylethoxymethyl, 4-methoxybenzyl, 3,4-dimethoxybenzyl, t-butyl, phthalamido, tetrahydropyranyl, tetrahydrofuranyl, methoxymethyl ether, methoxythiomethyl, trityl, pivalamido, t-butyldimethylsilyl, t-hexyldimethylsilyl, triisopropylsilyl, trichloroethoxycarbonyl, trifluoroacetyl, naphthoyl, formyl, acetyl; sulfonamides such as alkylsulfonamido and arylsulfonamido, and more preferred is pivalamido. Besides serving as an amino protecting group, the pivalamido protecting group increases the solubility of notoriously insoluble purine nucleobase derivatives and directs the N-glycosidic coupling of the purine bases to the 9 regioisomer as opposed to the 7 regioisomer.

Preferred hydroxy protecting groups (Z) for pyrimidine nucleobase derivatives are selected from silyl ether forming groups such as trialkylsilyl; carbamates such as t-butoxycarbonyl, benzyloxycarbonyl, 4-methoxybenzyloxycarbonyl and 4-nitrobenzyloxycarbonyl; carbocyclic esters such as formyl, acetyl, and pivalamido; preferred is trimethylsilyl. Preferred hydroxy protecting groups (Z) for purine nucleobase derivatives are selected from the group consisting of ether forming groups such as benzyl, t-butyl, trityl, tetrahydropyranyl, tetrahydrofuranyl, methoxymethyl, trityl; esters such as formyl, acetylpropionyl, pivalamido, benzoyl, substituted benzoyl; carbonates such as carbobenzoxy, t-butoxycarbonyl, carbethoxy, vinyloxycarbonyl; carbamates, such as N,N-dialkylcarbamoyl; trialkylsilyl ethers such as t-butyltrimethylsilyl, t-hexyldimethylsilyl, triisopropylsilyl; more preferred is pivalamido.

In providing protecting groups to form the nucleobase derivatives of the present invention, the protecting group itself may be protected. For example, N-acetylcytosine may be protected with trimethylsilyl to give bis-trimethylsilyl-N-acetylcytosine.

In addition, it is often advisable to convert any keto oxygen atoms on the nucleobase derivative to enol form. This makes the nucleobase derivative more aromatic and enchances the reactivity of the nucleobase derivative with the alpha-anomer enriched carbohydrate of formulas II and V. It is most convenient to enolize the keto oxygens and provide silyl protecting groups for them. In a preferred embodiment of the present invention, the nucleobase derivative (R'') employed is of the formula

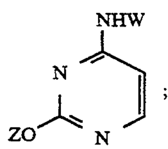

wherein Z and W are trimethylsilyl.

The solvents used to prepare the nucleobase derivative may be removed before the nucleoside derivative is employed in the glycosylation reaction or admixed with the reaction solvent provided the solvent admixture is inert to the glycosylation reaction.

The reaction solvent used in present glycosylation process must be inert to the glycosylation reaction conditions and have a boiling point temperature above about 70° C. Preferred reaction solvents are polar, non-nucleophilic solvents selected from the group consisting of anisole, acetonitrile, propionitrile, dioxane, glyme, and mixtures thereof; more preferred are acetonitrile, propionitrile, and mixtures thereof.

The present process employs a catalytic amount of salts that are substantially soluble in the solvent, highly ionized, and contain a non-nucleophilic anion. Preferred salts are selected from the group consisting of potassium, barium, cesium and trialkylammonium salts of trifluoromethanesulfonic acid, nanofluorobutanesulfonic acid, sulfuric acid, perchloric acid, nitric acid, and trifluoroacetic acid; more preferred are potassium or cesium salts of trifluoromethanesulfonic acid.

The catalyst employed in the present process offers process advantages over the glycoslation process described in Pending U.S. patent application Ser. No. 07/902,302, and include: a substantial reduction in the amount of nucleobase derivative required, an increase in nucleoside stereoselectivity, lower processing cost, an increase in processing through-put, a simplified process for separating the nucleoside product from the reaction mixture, and lower reaction temperatures, which further allows the employment less thermally stable carbohydrates in the glycoslation process.

In accordance with the present invention, nucleobase derivative (R'') employed must be equimolar relative to the amount of carbohydrate employed. However, it is more preferable to use an excess of nucleobase derivative in an amount ranging from about 3 molar equivalents to 30 molar equivalents, and more preferably from about 10 molar equivalents to 15 molar equivalents; and most preferably from about 10 molar equivalents to about 12 molar equivalents.

In preparing the alpha-anomer enriched nucleosides by the present process a smaller amount of nucleobase derivative may be employed ranging from about 1.5 molar equivialents to about 10 molar equivalents.

Although not critical, it is advisable that the reaction between the alpha-anomer enriched carbohydrate of formulas II and V and the nucleobase derivative be carried out in a dry atmosphere, e.g. of dry air, nitrogen or argon. This is because certain nucleobase derivatives such as silylated nucleobase derivatives, are moisture sensitive.

The glycosylation reaction temperature employed in the present invention ranges from about 50° C. to about 100° C.; however, about 75° C. to about 90° C. is preferred. The glycosylation reaction is preferably carried out under atmospheric pressure and is substantially complete in about 30 minutes to about 48 hours.

The progress of the present glycosylation process may be followed by procedures well known to one of ordinary skill in the art such as high performance liquid chromatography (HPLC) or thin layer chromatography (TLC) which can be used to detect the presence of the nucleoside product.

In accordance with the present glycosylation process, the beta-anomer enriched nucleosides are prepared in an alpha to beta anomeric ratio greater than 1:1 to about 1:9. On the other hand, the alpha-anomer enriched nucleosides of formulas I and IV are prepared in a alpha to beta anomeric ratio from about 1:1 to about 1:60.

The final phase of the reaction sequence is the removal of the protecting groups X, Z and/or W from the blocked nucleoside of formula I or IV. The same anomeric ratio of unprotected nucteoside is obtained by removal of the protecting groups.

Most silyl and silyl-amino protecting groups are easily cleaved by use of a protic solvent, such as water or an alcohol. The acyl protecting groups, such as benzoyl and the acyl-amino protecting groups, are removed by hydrolysis with a strong base at a temperature from about 0° C. to about 100° C. Strong or moderately strong bases suitable for use in this reaction are bases which have a pKa (at 25° C.) of about 8.5 to about 20.0. Such bases include alkali metal hydroxides such as sodium or potassium hydroxide; alkali metal alkoxides such as sodium methoxide or potassium t-butoxide; alkali metal amides; amines such as diethylamine, hydroxylamine, ammonia and the like; and other common bases such as hydrazinc and the like. At least one equivalent of base is needed for each protecting group.

The acyl protecting groups can also be removed with acid catalysts, such as methanesulfonic acid, hydrochloric acid, hydrobromic acid, sulfuric acid, or with acidic ion exchange resins. It is preferred to carry out such hydrolysis at relatively high temperature, such as the reflux temperature of the mixture, but temperatures as low as ambient may be used when particularly strong acids are used.

The removal of ether protecting groups is carried out by known methods, for example, with ethanethiol and aluminum chloride.

The t-butytdimethylsilyl protecting group requires acid conditions, such as contact with gaseous hydrogen halide, for its removal.

Removal of the protecting groups may be conveniently carried out in alcoholic solvents, especially aqueous alkanols such as methanol. However, the deblocking reaction may also be carried out in any convenient solvent, such as polyols including ethylene glycol, ethers such as tetrahydrofuran, ketones such as acetone and methyl ethyl ketone, or dimethylsulfoxide.

In a preferred embodiment, the deblocking reaction employs ammonia to remove a benzoyl hydroxy-protecting group at a temperature of about 10° C. It is preferable, however, to use an excess of base in this reaction, although the amount of excess base used is not crucial.

The resulting beta- and alpha-anomer enriched nucleosides of Formula VI and VII may be extracted and/or isolated from the reaction mixture by the procedure described in U.S. Pat. No. 4,965,374, which is incorporated herein by reference.

The following examples illustrate specific aspects of the present invention and are not intended to limit the scope thereof in any respect and should not be so construed.

EXAMPLE 1

Preparation of Bis-trimethylsilylcytosine

Cytosine (12.0 g), hexamethyldisilazane (60 ml) and ammonium sulfate (10 mg) were refluxed at 125° C. for 30 minutes to form a homogenous solution. The hexamethyldisilazane was removed by distillation to form the titled product.

EXAMPLE 2

Preparation of beta-anomer enriched 1-(2′-deoxy-2′,2′-difluoro-3′,5′-di-O-benzoyl-D-ribofuranosyl)-4-amino-pyrimidin-2-one 2-deoxy-2′,2′-difluoro-D-ribofuranosyl-3,5-dibenzoyl-1-α-methanesulfonate (1.15 g) was reacted with bis-trimethylsilylcytosine (6.89 g, 10 eq.) prepared as described in Example 1 in anisole (2 ml) and acetonitrile (3 ml) at 80° C. in the presence of the potassium salt of nanofluoro-1-butanesulfonic acid (0.5 g) for 16 hours. HPLC analysis confirmed completion of the reaction and indicated an in-situ yield of 33 percent. The beta to alpha anomer ratio of the titled compound was 3:1.

EXAMPLE 3

Preparation of beta-anomer enriched 1-(2′-deoxy2′,2′-difluoro-3′,5′-di-O-benzoyl-D-ribofuranosyl)-4-amino-pyrimidin-2-one with potassium sulfate 2-deoxy-2,2-difluoro-D-ribofuranosyl-3,5-dibenzoyl-1-α-methanesulfonate (1.15 g) was reacted with the bis-trimethylsilylcytosine (6.89 g, 10 eq.) prepared as described in Example 1 in acetonitrile (2.0 ml) at 80° C. in the presence of potassium sulfate (0.5 g) for 72 hours. HPLC analysis confirmed completion of the reaction and indicated an in-situ yield of 65 percent. The beta to alpha anomer ratio of the titled compound was 4.7:1.

EXAMPLE 4

Preparation of beta-anomer enriched 1-(2′-deoxy-2′2′-difluoro-3′,5′-di-O-benzoyl-D-ribofuranosyl)-4-amino-pyrimidin-2-one with the tetrabutylammonium salt of trifluoromethanesulfonic acid 2-deoxy-2,2-difluoro-D-ribofuranosyl-3,5-dibenzoyl-1-α-methanesulfonate (0.29 ml) was reacted with the bis-trimethylsilylcytosine (6.89 g, 10 eq.) prepared as described in Example 1 in acetonitrile (3.0 ml) at 80° C. in the presence of the tetrabutylammonium salt of trifluoromethanesulfonic acid (1.5 mmol) (prepared in-situ by treating tetrabutylammonium hydroxide (1.5 ml of a 1 molar solution in methanol) with trifluoromethanesulfonic acid (0.13 ml)), then distilling to remove the methanol) for 4 hours. HPLC analysis confirmed completion of the reaction and indicated an in-situ yield of 45 percent. The beta to alpha anomer ratio of the titled compound was 7.1:1

EXAMPLE 5

Preparation of beta-anomer enriched 1-(2′-deoxy-2′,2′-difluoro-3′,5′-di-O-benzoyl-D-ribofuranosyl)-4-amino-pyrimidin-2-one with barium sulfate 2-deoxy-2,2-difluoro-D-ribofuranosyl-3,5-dibenzoyl-1-α-methanesulfonate (1.15 g) was reacted with bis-trimethylsilylcytosine (6.89 g, 10 eq.) prepared as described in Example 1 in acetonitrile (3.0 ml) at 75° C. in the presence of barium sulfate (1.0 g) for 20.5 hours. HPLC analysis indicated an in-situ yield of 36 percent. The beta to alpha anomer ratio of the titled compound was 11.2:1

EXAMPLE 6

Preparation of beta-anomer enriched 1-(2′-deoxy-2′,2′-difluoro-3′,5′-di-O-benzoyl-D-ribofuranosyl)-4-amino-pyrimidin-2-one with cesium sulfate 2-deoxy-2,2-difluoro-D-ribofuranosyl-3,5-dibenzoyl-1-α-methanesulfonate (1.15 g) was reacted with bis-trimethylsilylcytosine (6.89 g, 10 eq.) prepared as described in Example 1 in acetonitrile (3.0 ml) at 75° C. in the presence of cesium sulfate (1.0 g) for 21 hours. HPLC analysis indicated an in-situ yield of 24 percent. The beta to alpha anomer ratio of the titled compound was 14.9:1

EXAMPLE 7

Preparation of beta-anomer enriched 1-(2′-deoxy-2′,2′-difluoro-3′,5′-di-O-benzoyl-D-ribofuranosyl)-4-amino-pyrimidin-2-one with the cesium salt of trifluoromethane sulfonic acid.

2-deoxy-2,2-difluoro-D-ribofuranosyl-3,5-dibenzoy-1-α-methanesulfonate (1.15 g) was reacted with bis-trimethylsilylcytosine (6.89 g, 10 eq.) prepared as described in Example 1 in acetonitrile (3.0 ml) at 75° C. in the presence of the cesium salt of trifluoromethanesulfonic acid (prepared in-situ by treating of 0.13 ml of trifluoromethane sulfonic acid with excess cesium carbonate) for 20.5 hours. HPLC analysis confirmed completion of the reaction and indicated an in-situ yield of 65 percent. The beta to alpha anomer ratio of the titled compound was 7.2:1

EXAMPLE 8

Preparation of beta-anomer enriched 1-(2′-deoxy-2′,2′-difluoro-3′,5′-di-O-benzoyl-D-ribofuranosyl)-4-amino-pyrimidin-2-one with the barium salt of trifluoromethanesulfonic acid 2-deoxy-2,2-difluoro-D-ribofuranosyl-3,5-dibenzoyl-1-α-methanesulfonate (1.15 g) was reacted with bis-trimethylsilylcytosine (6.89 g, 10 eq.) prepared as described in Example 1 in acetonitrile (3.0 ml) at 75° C. in the presence of the barium salt of trifluoromethanesulfonic acid (prepared in-situ by treating of 0.13 ml of trifluoromethanesulfonic acid with excess barium carbonate) for 20.5 hours. HPLC analysis indicated an in-situ yield of 25 percent. The beta to alpha anomer ratio of the titled compound was 14.4:1

EXAMPLE 9

Preparation of beta-anomer enriched 1-(2'-deoxy-2',2'-difluoro-3',5'-di-O-benzoyl-D-ribofuranosyl)-4-amino-pyrimidin-2-one with the potassium salt of trifluoromethanesulfonic acid 2-deoxy-2,2-difluoro-D-ribofuranosyl-3,5-dibenzoyl-1-α-methanesulfonate (2.3 g, 12.6 eq.) was reacted with bis-trimethylsilylcytosine (16.1 g) prepared as described in Example 1 in acetonitrile (8.0 ml) at 75° C. and in the presence of the potassium salt of trifluoromethanesulfonic acid (prepared in-situ by treating trifluoromethanesulfonic acid (0.26 ml) with potassium carbonate (1.0 g)) for 45 hours. HPLC analysis indicated an in-situ yield of 69.8 percent. The beta to alpha anomer ratio of the titled compound was 7.2:1.

To extract the nucleoside product, the reaction mixture was cooled between 70° C. and 80° C. and combined with 40 ml of 4 N hydrochloric acid. The product precipitated, was filtered, and dried. A quantitative HPLC analysis indicated an isolated yield of 62.4 percent.

EXAMPLE 10

Preparation of beta-anomer enriched 1-(2'-deoxy2',2'-difluoro-3',5'-di-O-benzoyl-D-ribofuranosyl)-4-amino-pyrimidin-2-one with the potassium salt of trifluoromethanesulfonic acid 2-deoxy-2,2-difluoro-D-ribofuranosyl-3,5-dibenzoyl-1-α-methanesulfonate (2.3 g) was reacted with bis-trimethylsilylcytosine (16.1 g, 12.6 eq.) prepared as described in Example 1 in propionitrile (8.0 ml) at 90° C. and in the presence of the potassium salt of trifluoromethanesulfonic acid (prepared in-situ by treating trifluoromethanesulfonic acid (0.26 ml) with potassium carbonate (1.0 g)) for 21 hours. HPLC analysis confirmed completion of the reaction. The beta to alpha anomer ratio of the titled compound was 6.7:1.

To extract the nucleoside product, the reaction mixture was cooled between 70° C. and 80° C. and combined with 40 ml of 4 N hydrochloric acid. The product precipitated, was filtered, and dried. A quantitative HPLC analysis indicated an isolated yield of 59.3 percent.

EXAMPLE 11

Preparation of alpha-anomer enriched 1-(2'-deoxy-2',2'-difluoro-3',5'-di-O-benzoyl-D-ribofuranosyl)-4-amino-pyrimidin-2-one with the potassium salt of trifluoromethanesulfonic acid 2-deoxy-2,2-difluoro-D-ribofuranosyl-3,5- dibenzoyl-1-α-methanesulfonate (1.15 g) was reacted with bis-trimethylsilylcytosine (8.1 g, 12.6 eq.) prepared as described in Example 1 in propionitrile (6.0 ml) at 90° C. and in the presence of the potassium salt of trifluoromethanesulfonic acid. (prepared in-situ by treating trifluoromethanesulfonic acid (0.08 ml) with potassium carbonate (0.5 g)) for 21 hours. HPLC analysis confirmed completion of the reaction and indicated an in-situ yield of 87.6 percent. The alpha to beta anomer ratio of the titled compound was 58.4:1.

COMPARATIVE EXAMPLE 12

Preparation of beta-anomer enriched 1-(2'-deoxy-2',2'-difluoro-3',5'-di-O-benzoyl-D-ribofuranosyl)-4-amino-pyrimidin-2-one without a catalyst 2-deoxy-2,2-difluoro-D-ribofuranosyl-3,5-dibenzoyl-1-α-methanesulfonate (1.15 g) was reacted with bis-trimethylsilylcytosine (6.09 g, 10 eq.) prepared as described in Example 1 in anisole (4 ml) at 110° C. for 20 hours. HPLC analysis confirmed completion of the reaction and indicated an in-situ yield of 77 percent. The beta to alpha anomer ratio of the titled compound was 3.4:1.

COMPARATIVE EXAMPLE 13

Preparation of beta-anomer enriched 1-(2'deoxy-2',2'-difluoro-3',5'-di-O-benzoyl-D-ribofuranosyl)-4-amino-pyrimidin-2-one without a catalyst 2-deoxy-2,2-difluoro-D-ribofuranosyl-3,5-dibenzoyl-1-α-methanesulfonate (1.15 g) was reacted with bis-trimethylsilylcytosine (6.08 g, 10 eq.) prepared as described in Example 1 in propionitrile (4 ml) at 85° C. in the presence of the cesium salt of trifluoromethanesulfonic acid (prepared in-situ by treating trifluoromethanesulfonic acid (0.13 ml) with excess cesium carbonate) for 20 hours. HPLC analysis confirmed completion of the reaction and indicated an in-situ yield of 70 percent. The beta to alpha anomer ratio of the titled compound was 6.7:1.

The present invention has been described in detail, including the preferred embodiments thereof. However, it will be appreciated that those skilled in the art, upon consideration of the present disclosure, may make modifications and/or improvements on this invention that fall within the scope and spirit of the invention as set forth in the following claims.

What is claimed is:

1. A catalytic stereoselective glycosylation process for preparing a beta-anomer enriched nucleoside of the formula

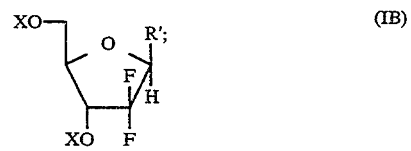

wherein each X is independently selected from hydroxy protecting groups and R' is a nucleobase selected from the group consisting of

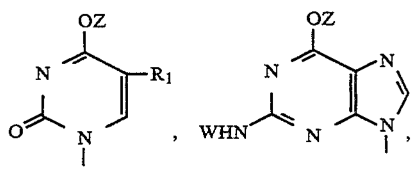

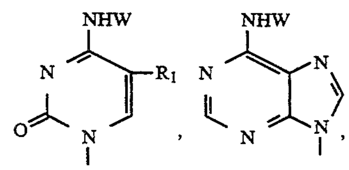

-continued

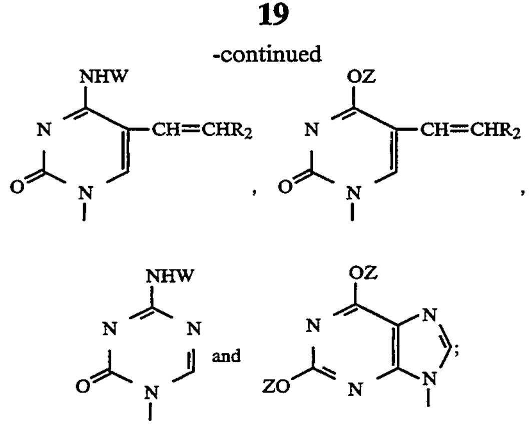

wherein $R_1$ is selected from the group consisting of hydrogen, $C_1$–$C_7$ alkyl and halo; $R_2$ is selected from the group consisting of hydrogen, $C_1$–$C_7$ alkyl and halo; Z is a hydroxy protecting group and W is an amino protecting group; comprising reacting alpha-anomer 2,2-difluorocarbohydrate in a anomer ratio of greater than 1:1 alpha to beta of the formula

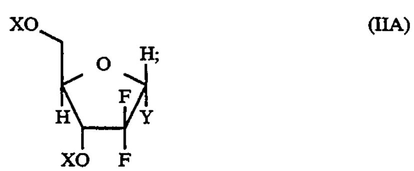

(IIA)

wherein Y is selected from the group consisting of optionally substituted $C_1$–$C_7$ alkylsulfonyloxy and optionally substituted arylsulfonyloxy, where the substituents can be one or two groups selected from cyano, halo, carboalkoxy, toluoyl, nitro, alkoxy, $C_1$–$C_7$ alkyl, and di($C_1$–$C_7$ alkyl)amino, aryl is phenyl or naphthyl, and X is as defined above; with at least 3 molar equivalents of a nucleobase derivative, R″, selected from the group consisting of

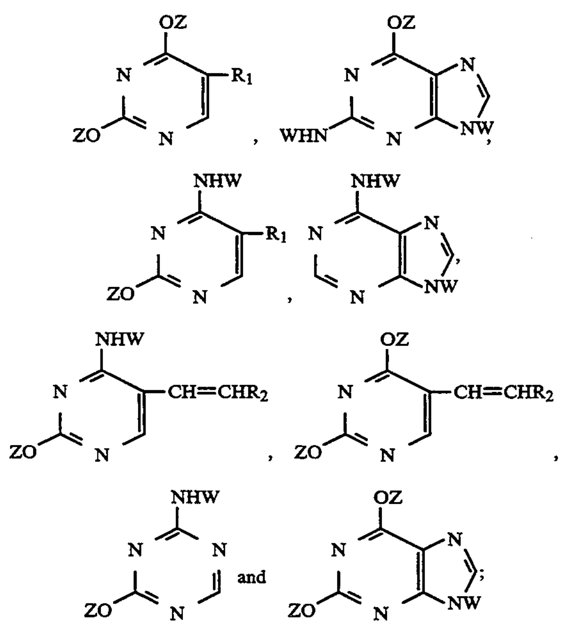

wherein $R_1$, $R_2$, Z and W are as defined above; at a temperature ranging from about 50° C. to about 100° C.; in an inert solvent; and in the presence of a catalyst selected from the group consisting of the potassium, barium, cesium, and trialkylammonium salts of trifluoromethanesulfonic acid, nanofluorobutanesulfonic acid, sulfuric acid, perchloric acid, nitric acid, and trifluoroacetic acid.

2. The process of claim 1 wherein the amount of R″ is about 3 molar equivalents to about 20 molar equivalents.

3. The process of claim 1 wherein Y is selected from the group consisting of methanesulfonyloxy, 2-chloro-1-ethanesulfonyloxy, toluenesulfonyloxy, p-nitrobenzenesulfonyloxy and p-bromobenzenesulfonyloxy.

4. The process of claim 1 wherein X is selected from the group consisting of mono-substituted benzoyl, di-substituted benzoyl and benzoyl.

5. The process of claim 1 wherein Z and W are selected from the group consisting of trialkylsilyl, t-butoxycarbonyl, benzyloxycarbonyl, 4-methoxybenzyloxycarbonyl, 4-nitrobenzyloxycarbonyl, formyl and acetyl.

6. The process of claim 1 wherein the solvent is selected from polar, non-nucleophilic solvents.

7. The process of claim 6 wherein the solvent is selected from the group consisting of anisole, acetonitrile, propionitrile, dioxane, glyme, and mixtures thereof.

8. The process of claim 1 wherein R″ is of the formula

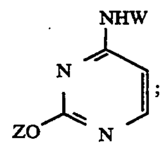

wherein Z and W are trimethylsilyl

9. The process of claim 8 wherein the amount of R″ ranges from about 3 molar equivalents to about 20 molar equivalents.

10. The process of claim 8 wherein Y is methanesulfonyloxy.

11. The process of claim 8 wherein X is benzoyl.

12. The process of claim 8 wherein the solvent ms selected from polar, nonnucleophilic solvents.

13. The process of claim 8 wherein the catalyst is selected from highly ionized salts that are substantially soluble in the solvent, and contain a non-nucleophilic anion.

14. The process of claim 8 wherein the reaction temperature is from about 75° C. to about 100° C.

15. The process of claim 1 further comprising deblocking to form a beta-anomer enriched nucleoside of the formula

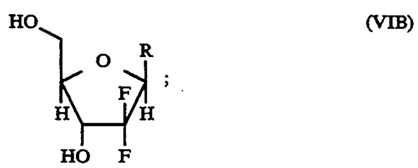

(VIB)

wherein R is a deblocked nucleobase selected from the group consisting of

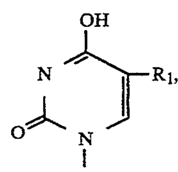

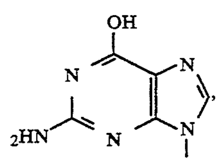

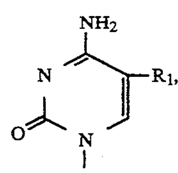

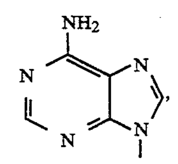

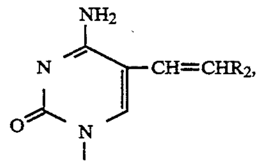

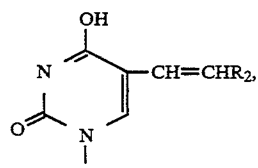

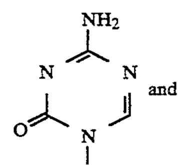

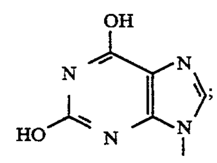

wherein $R_1$ is selected from the group consisting of hydrogen, alkyl and halo; and $R_2$ is selected from the group consisting of hydrogen, alkyl and halo.

16. The process of claim 15 wherein R is of the formula

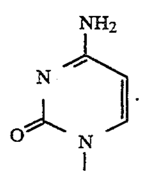

17. A catalytic stereoselective glycosylation process for preparing a beta-anomer enriched nucleoside of the formula

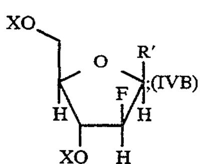

wherein each X is independently selected from hydroxy protecting groups and R' is a nucleobase selected from the group consisting of

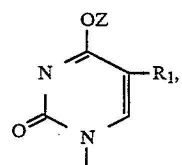

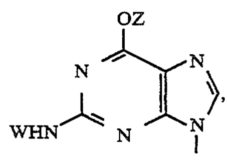

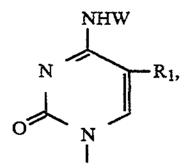

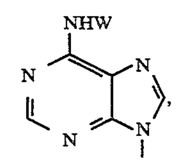

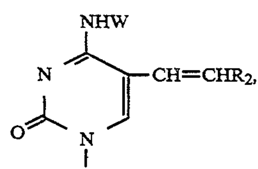

-continued

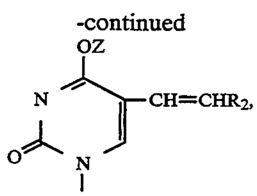

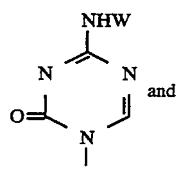

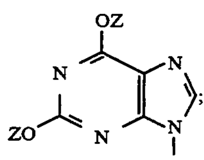

wherein $R_1$ is selected from the group consisting of hydrogen, $C_1$–$C_7$ alkyl and halo; $R_2$ is selected from the group consisting of hydrogen, $C_1$–$C_7$ alkyl and halo; Z is a hydroxy protecting group and W is an amino protecting group; comprising reacting alpha-anomer 2-fluorocarbohydrate in a anomer ratio of greater than 1:1 alpha to beta of the formula

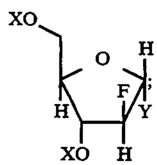

(VA)

wherein Y is selected from the group consisting of optionally substituted $C_1$–$C_7$ alkylsulfonyloxy and optionally substituted arylsulfonyloxy, where the substituents can be one or two groups selected from cyano, halo, carboalkoxy, toluoyl, nitro, alkoxy, $C_1$–$C_7$ alkyl, and di($C_1$–$C_7$ alkyl)amino, aryl is phenyl or naphthyl, and X is as defined above; with at least 3 molar equivalents of a nucleobase derivative, R", selected from the group consisting of

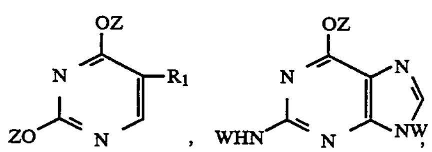

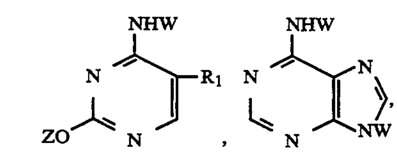

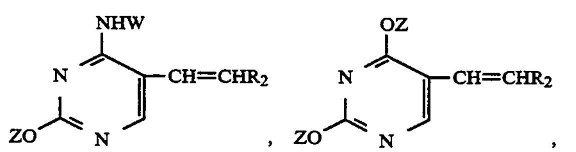

-continued

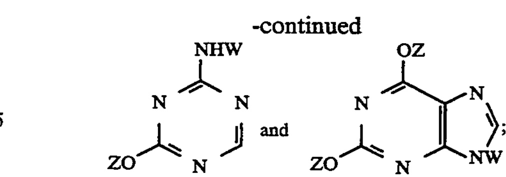

wherein $R_1$, $R_2$, Z and W are as defined above; at a temperature ranging from about 50° C. to about 100° C. in an inert solvent; and in the presence of catalyst selected from the group consisting of the potassium, barium, cesium, and trialkylammonium salts of trifluoromethanesulfonic acid, nanofluorobutanesulfonic acid, sulfuric acid, perchloric acid, nitric acid, and trifluoroacetic acid.

18. The process of Claim 17 wherein the amount of R" is about 3 molar equivalents to about 20 molar equivalents.

19. The process of claim 17 wherein Y is selected from the group consisting of methanesulfonyloxy, 2-chloro-1-ethanesulfonyloxy, toluenesulfonyloxy, pnitrobenzenesulfonyloxy and p-bromobenzenesulfonyloxy.

20. The process of claim 17 wherein X is selected from the group consisting of mono-substituted benzoyl, di-substituted benzoyl and benzoyl.

21. The process of claim 17 wherein Z and W are selected from the group consisting of trialkylsilyl, t-butoxycarbonyl, benzyloxycarbonyl, 4-methoxybenzyloxycarbonyl, 4-nitrobenzyloxycarbonyl, formyl and acetyl.

22. The process of claim 17 wherein the solvent is selected from polar, non-nucleophilic solvents.

23. The process of claim 22 wherein the solvent is selected from the group consisting of anisole, acetonitrile, propionitrile, dioxane, glyme, and mixtures thereof.

24. The process of claim 17 further comprising deblocking to form a beta-anomer enriched nucleoside of the formula

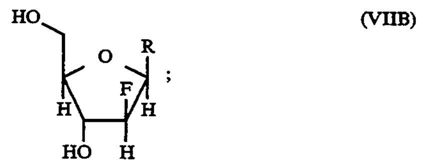

wherein R is a deblocked nucleobase selected from the group consisting of

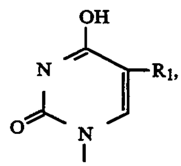

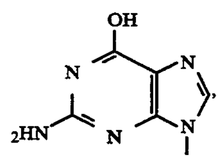

-continued
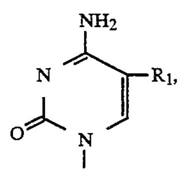
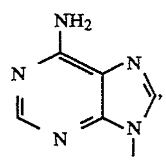
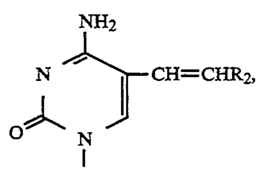
-continued
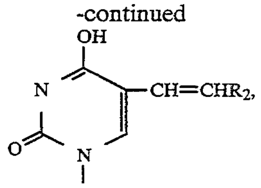
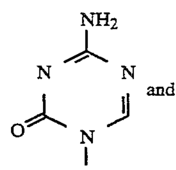
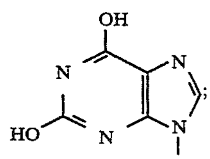
wherein $R_1$ is selected from the group consisting of hydrogen, alkyl and halo; and $R_2$ is selected from the group consisting of hydrogen, alkyl and halo.
* * * * *